US009707194B2

(12) United States Patent
Tsuru et al.

(10) Patent No.: US 9,707,194 B2
(45) Date of Patent: Jul. 18, 2017

(54) KETOPROFEN-CONTAINING POULTICE (71) Applicant: HISAMITSU PHARMACEUTICAL CO., INC., Tosu-shi, Saga (JP)

(72) Inventors: Seiichiro Tsuru, Tosu (JP); Masayoshi Maki, Tosu (JP); Shinji Yamasoto, Tosu (JP); Takaaki Terahara, Tosu (JP)

(73) Assignee: HISAMITSU PHARMACEUTICAL CO., INC., Tosu-Shi, Saga (JP)

( * ) Notice: Subject to any disclaimer, the term of this patent is extended or adjusted under 35 U.S.C. 154(b) by 0 days.

(21) Appl. No.: 15/121,534

(22) PCT Filed: Feb. 26, 2015

(86) PCT No.: PCT/JP2015/055616
§ 371 (c)(1),
(2) Date: Aug. 25, 2016

(87) PCT Pub. No.: WO2015/129808
PCT Pub. Date: Sep. 3, 2015

(65) Prior Publication Data
US 2016/0361281 A1 Dec. 15, 2016

(30) Foreign Application Priority Data
Feb. 27, 2014 (JP) ................................. 2014-036618

(51) Int. Cl.
A61K 31/192 (2006.01)
A61K 9/00 (2006.01)
A61K 9/70 (2006.01)
A61K 31/12 (2006.01)
A61K 47/10 (2017.01)
D03D 15/00 (2006.01)

(52) U.S. Cl.
CPC .......... *A61K 31/192* (2013.01); *A61K 9/0014* (2013.01); *A61K 9/7023* (2013.01); *A61K 9/7069* (2013.01); *A61K 31/12* (2013.01); *A61K 47/10* (2013.01); *D03D 15/00* (2013.01)

(58) Field of Classification Search
CPC ............................ A61K 9/0014; A61K 9/7038
See application file for complete search history.

(56) References Cited

U.S. PATENT DOCUMENTS

| | | | |
|---|---|---|---|
| 4,489,057 A | 12/1984 | Welters et al. | |
| 5,000,937 A | 3/1991 | Grollier et al. | |
| 5,000,945 A | 3/1991 | Kobayashi et al. | |
| 5,478,567 A | 12/1995 | Nakagawa et al. | |
| 5,637,293 A | 6/1997 | Honda | |
| 5,849,272 A | 12/1998 | Baba et al. | |
| 5,869,087 A | 2/1999 | Hirano et al. | |
| 5,989,528 A | 11/1999 | Tanner et al. | |
| 6,294,186 B1 | 9/2001 | Beerse et al. | |
| 6,455,067 B1 * | 9/2002 | Woo | A61K 9/7053 424/449 |
| 6,509,008 B1 | 1/2003 | Candau | |
| 6,528,068 B1 | 3/2003 | Yumioka et al. | |
| 6,914,169 B1 | 7/2005 | Oota et al. | |
| 2003/0044365 A1 | 3/2003 | Candau | |
| 2003/0124070 A1 | 7/2003 | Gonzalez et al. | |
| 2003/0149385 A1 | 8/2003 | Tsuruda et al. | |
| 2003/0157138 A1 | 8/2003 | Eini et al. | |
| 2004/0052738 A1 | 3/2004 | Candau | |
| 2005/0042269 A1 * | 2/2005 | Tateishi | A61F 13/023 424/449 |
| 2005/0053646 A1 | 3/2005 | Yasukochi et al. | |
| 2006/0198880 A1 | 9/2006 | Hashimoto et al. | |
| 2006/0263420 A1 | 11/2006 | Hirano et al. | |
| 2007/0148216 A1 | 6/2007 | Yoshitake et al. | |
| 2007/0154531 A1 | 7/2007 | Hashimoto et al. | |
| 2007/0269496 A1 | 11/2007 | Gamble | |
| 2007/0280980 A1 | 12/2007 | Hashimoto et al. | |
| 2008/0031835 A1 | 2/2008 | Kawamura et al. | |
| 2008/0292670 A1 | 11/2008 | Hirano et al. | |
| 2008/0317689 A1 | 12/2008 | Yoshitake et al. | |
| 2009/0028806 A1 | 1/2009 | Suzuki et al. | |
| 2010/0239639 A1 | 9/2010 | Suzuki et al. | |
| 2010/0249236 A1 | 9/2010 | Hirano et al. | |
| 2011/0028555 A1 * | 2/2011 | Kawamura | A61K 9/0014 514/567 |

FOREIGN PATENT DOCUMENTS

| | | |
|---|---|---|
| EP | 0 928 608 A2 | 7/1999 |
| EP | 1 234 573 A1 | 8/2002 |
| EP | 1 698 330 A1 | 9/2006 |
| FR | 2 804 024 A1 | 1/2000 |
| JP | 53-99316 A | 8/1978 |

(Continued)

OTHER PUBLICATIONS

ISR issued in corresponding international application No. PCT/JP2015/055616 mailed May 19, 2015.
Ryoichi Kamide, "Drug-Induced Photosensitivity—An Update", Photomedicine and Photobiology, vol. 21, 1999, pp. 9-10.
Fumikazu Yamazaki, Hiroko Hashimoto & Takeshi Horio, "Experimental Studies Phototoxicity, Phoallergencitiy and Prolonged Photosensitivity Due to Nonsteroidal Anti-Inflammatory Drugs (NSAIDs)", Jpn J Dermatol 113, 2003, pp. 405-411.
Kenji Sugibayashi, "External Preparation for Cutaneous Administration and Transdermal Absorption Drug", (Hifu Tekiyo Gaiyozai to Keihi Kyushugata Seizai), Editing: Committee for Lore of Pharmaceutical Technology, The Academy of Pharmaceutical Science and Technology, Japan, Publisher: Shoichiro Takeda, PUblishing office: Jiho Inc., May 20, 2013, pp. 207-219.
Junko Kano, "Functions and development of new UVA absorber", Fragrance Journal Jun. 2002, 2002, pp. 139-144.

(Continued)

*Primary Examiner* — Mark V Stevens
(74) *Attorney, Agent, or Firm* — Nath, Goldberg & Meyer; Joshua B. Goldberg; Tanya E. Harkins (57) ABSTRACT

The invention provides a gel patch comprising a support and an adhesive layer on the support, wherein the adhesive layer comprises 1.5 to 2.5 mass % of ketoprofen, 1.5 to 2.5 mass % of 4-tert-butyl-4'-methoxydibenzoylmethane and 12 to 18 mass % of propylene glycol, based on the total mass of the adhesive layer.

12 Claims, 2 Drawing Sheets

(56) References Cited

FOREIGN PATENT DOCUMENTS

| | | |
|---|---|---|
| JP | 56-22711 A | 3/1981 |
| JP | 60-155111 A | 8/1985 |
| JP | 1-149713 A | 6/1989 |
| JP | 1-158090 A | 6/1989 |
| JP | 7-126121 A | 5/1995 |
| JP | 9-151108 A | 6/1997 |
| JP | 9-169658 A | 6/1997 |
| JP | 9-291019 A | 11/1997 |
| JP | 11-246841 A | 9/1999 |
| JP | 11-343224 A | 12/1999 |
| JP | 2000-136122 A | 5/2000 |
| JP | 2001-328935 A | 11/2001 |
| JP | 2002-521417 A | 7/2002 |
| JP | 2003-12508 A | 1/2003 |
| JP | 2003-26559 A | 1/2003 |
| JP | 2003-55181 A | 2/2003 |
| JP | 2003-511474 A | 3/2003 |
| JP | 2003-528821 A | 9/2003 |
| JP | 2005-516921 A | 6/2005 |
| JP | 2007-151916 A | 6/2007 |
| JP | 2011-162514 A | 8/2011 |
| WO | 93/04677 A1 | 3/1993 |
| WO | 96/08245 A1 | 3/1996 |
| WO | 00/06110 A1 | 2/2000 |
| WO | 01/68061 A1 | 9/2001 |
| WO | 03/062342 A1 | 7/2003 |
| WO | 2004/098575 A1 | 11/2004 |
| WO | 2005/023307 A1 | 3/2005 |
| WO | 2005/063215 A1 | 7/2005 |
| WO | 2005/110482 A1 | 11/2005 |
| WO | 2005/123136 A1 | 12/2005 |
| WO | 2006/090833 A1 | 8/2006 |
| WO | 2006/090839 A1 | 8/2006 |
| WO | 2006/095820 A1 | 9/2006 |
| WO | 2008/133272 A1 | 11/2008 |

OTHER PUBLICATIONS

J.A. Cordero, M. Camacho, R. Obach, J. Domenech, L. Vila, "In vitro based index of topical anti-inflammatory activity to compare a series of NSAIDs", European Journal of Pharmaceutics and Biopharmaceutics 51, 135-142, 2001, pp. 135-142.

Tadashi Sakurai, Kanchiro Saito, "Performance and development of the ultrafine zinc oxide as UV shielding agent", Fragrance Journal May 1995, 1999, pp. 79-83.

Toshio Demitsu, "Photocontact dermatitis due to nonsteroidal anti-inflammatory external preparations", The Allergy in Practice 15(9), 1995, pp. 621-622.

"Recent External Preparations for Skin (Saikin no Hihu Gaiyozai)", Nanzando Co., Ltd., Oct. 7, 1991, pp. 195-198.

A. Radshuweit, H.-H. Ruttinger, P. Nuhn, W. Wohlrab & Chr. Huschka, "UV-Induces Formation of Hydrogen Peroxide Based on the Photochemistry of Ketoprofen", Photochemistry and Photobiology, 73(2), 2001, pp. 119-127.

Form PCT/IB/338 issued in corresponding application No. PCT/JP2015/055616 mailed Sep. 9, 2016.

Form PCT/IB/373 issued in corresponding application No. PCT/JP2015/055616 issued Aug. 30, 2016.

Form PCT/ISA/237 issued in corresponding application No. PCT/JP2015/055616 mailed May 19, 2015.

Ishiguro, Fumiko, et al "Deciding on a Cataplasm Formulation by Means of Multipurpose Simultaneous Optimization" Therapeutic Research, vol. 15, No. 10, Symposium: 7th Transdermal Therapeutic System Symposium, Poster Session 14, 1994, p. 3887-p. 3888.

H. Okuyama,et al "Influence of non-ionic surfactants, pH and propylene glycol on percutaneous absorption of piroxicam from cataplasm", International Journal of Pharmaceutics, vol. 186, 1999, p. 141-p. 148.

Office Action dated Apr. 11, 2017 in corresponding counterpart Japanese Patent Application No. P2016-505295.

* cited by examiner

KETOPROFEN-CONTAINING POULTICE

TECHNICAL FIELD

The present invention relates to a ketoprofen-containing gel patch.

BACKGROUND ART

Non-steroidal anti-inflammatory analgesics such as ketoprofen have excellent anti-inflammatory and analgesic effects and are therefore included as drug components in various forms of transdermal preparations including patches such as gel patches and plasters, as well as gels, creams, ointments, liniments and the like. However, when a transdermal preparation is used that contains, as an active ingredient, a non-steroidal anti-inflammatory analgesic which is a photosensitive compound, photodermatosis is developed as a side-effect, in some rare cases.

Skin irritation such as photodermatosis is a sensitive dermatitis symptom, including erythema with itching or eruption, due to exposure of a photosensitive compound such as ketoprofen to ultraviolet rays. In order to reduce the risk of such side-effects it is desirable to limit outdoor activities or to shield the entire transdermal preparation, so as to avoid exposure to ultraviolet rays.

In order to help prevent occurrence of photodermatosis, it has been attempted in recent years to develop ketoprofen-containing tape preparations containing ultraviolet absorbers with a high degree of skin migration (see PTL 1), or gel patches provided with supports modified so as to shield ultraviolet rays (see PTL 2). Presumably, by minimizing photodecomposition of ketoprofen and reducing production of ketoprofen decomposition products it is possible to minimize occurrence of side-effects such as photodermatosis.

CITATION LIST

Patent Literature

[PTL 1] WO2006/090833
[PTL 2] WO01/068061

SUMMARY OF INVENTION

Technical Problem

In general, gel patches have high water contents compared to tape preparations and therefore more powerful cooling effects, but the drug absorption rates of gel patches are lower than those of tape preparations. One possible method to increase the drug effect of a ketoprofen-containing gel patch to the level of the drug effect of a ketoprofen-containing tape preparation, is to increase the ketoprofen content of the gel patch. However, increasing the ketoprofen content can potentially increase the probability of occurrence of side-effects. It is therefore an object of the present invention to provide a ketoprofen-containing gel patch that has excellent pharmacological action while maintaining a low level of occurrence of side-effects.

Solution to Problem

The present inventors examined ketoprofen-containing gel patches in light of the situation described above. As a result, the present inventors found that with a gel patch obtained by simply increasing the ketoprofen content in the construction of a conventional gel patch, the skin permeation of ketoprofen does not increase. Furthermore, the present inventors found that if the ketoprofen content is increased and propylene glycol is added, the degree of skin permeation of ketoprofen in the gel patch can be increased to be equivalent or greater than the degree of skin permeation of ketoprofen in a tape preparation. The present inventors further found that 4-tert-butyl-4'-methoxydibenzoylmethane (also referred to as "BM-DBM") which can reduce skin irritation of ketoprofen, has higher skin migration in a gel patch than in a tape preparation.

Based on these findings, the present inventors found that the problems described above can be solved by a gel patch containing ketoprofen, 4-tert-butyl-4'-methoxydibenzoylmethane and propylene glycol in a specific ratio.

That is, the present invention provides a gel patch comprising a support and an adhesive layer on the support, wherein the adhesive layer comprises 1.5 to 2.5 mass % of ketoprofen, 1.5 to 2.5 mass % of 4-tert-butyl-4'-methoxydibenzoylmethane and 12 to 18 mass % of propylene glycol, based on the total mass of the adhesive layer.

Also, the adhesive layer preferably further comprises 12 to 18 mass % of D-sorbitol based on the total mass of the adhesive layer. The compound D-sorbitol increases the effect of 4-tert-butyl-4'-methoxydibenzoylmethane and further inhibits photodecomposition of ketoprofen.

In addition, the support is preferably a knitted fabric having a thickness of 450 to 650 μm.

Advantageous Effects of Invention

The ketoprofen-containing gel patch of the invention improves the skin permeability of ketoprofen and can exhibit excellent pharmacological action, while inhibiting occurrence of skin irritation and the like.

DESCRIPTION OF EMBODIMENTS

A ketoprofen-containing gel patch as an embodiment of the invention will now be explained in detail.

Throughout the present specification, "skin reaction" means skin irritation that appears as a photodermatosis due to ketoprofen.

The ketoprofen-containing gel patch as an embodiment of the invention is a gel patch comprising a support and an adhesive layer on the support, the adhesive layer comprising 1.5 to 2.5 mass % of ketoprofen, 1.5 to 2.5 mass % of 4-tert-butyl-4'-methoxydibenzoylmethane (hereunder also referred to as "BM-DBM") and 12 to 18 mass % of propylene glycol, based on the total mass of the adhesive layer.

The support of this embodiment is preferably a nonwoven fabric or knitted fabric, and most preferably a nonwoven fabric or knitted fabric having a prescribed elongation recovery rate. The elongation recovery rate referred to here is the value measured according to "JIS L 1096:2010 Testing Methods for Woven and Knitted Fabrics". Using a nonwoven fabric or knitted fabric having a prescribed elongation recovery rate is preferred because, when applied to moving parts such as joints, the support will stretch in response to movement of the site of application. The support may have an elongation recovery rate of 70 to 90% or 73 to 98% after 50% elongation.

When a woven fabric is used as the support, a knitted fabric may be used that has been processed into a sheet with assembly by circular knit, warp knit, weft knit or the like as the stitch form. Knitted fabrics are largely classified as weft knitted fabrics or warp knitted fabrics, and weft knitted fabrics include those formed by plain stitch (or jersey stitch), rib stitch, purl stitch (garter stitch) and smooth stitch (interlock stitch). Warp knitted fabrics include those formed by denbigh stitch, vandyke stitch, cord stitch, atlas stitch and multiaxial inlay stitch. Any of such knitted fabrics may be suitably used, although a plain stitch knitted fabric is especially preferred. Preferred examples of knitted fabrics include knitted fabrics comprising combinations of one or more materials from among polyester-based, nylon-based, polypropylene-based and rayon-based materials, among which knitted fabrics made of polyethylene terephthalate materials are more preferred as they have low interaction with drugs.

Furthermore, when the support is a knitted fabric or nonwoven fabric, and a water-containing adhesive mass is spread over a woven fabric, the components in the adhesive layer or the components that become oozed by syneresis from the adhesive layer may sometimes seep through the woven fabric stitches, and therefore the basis weight of a knitted fabric is preferably 80 to 150 g/m² and more preferably 95 to 125 g/m². If the basis weight is within this range, the components contained in the adhesive layer or the components freed by separation from the adhesive layer will tend to be able to spread without seeping through the gaps of the base fabric, and it will be possible to maintain anchorage between the base fabric and the adhesive mass.

Figure 1:
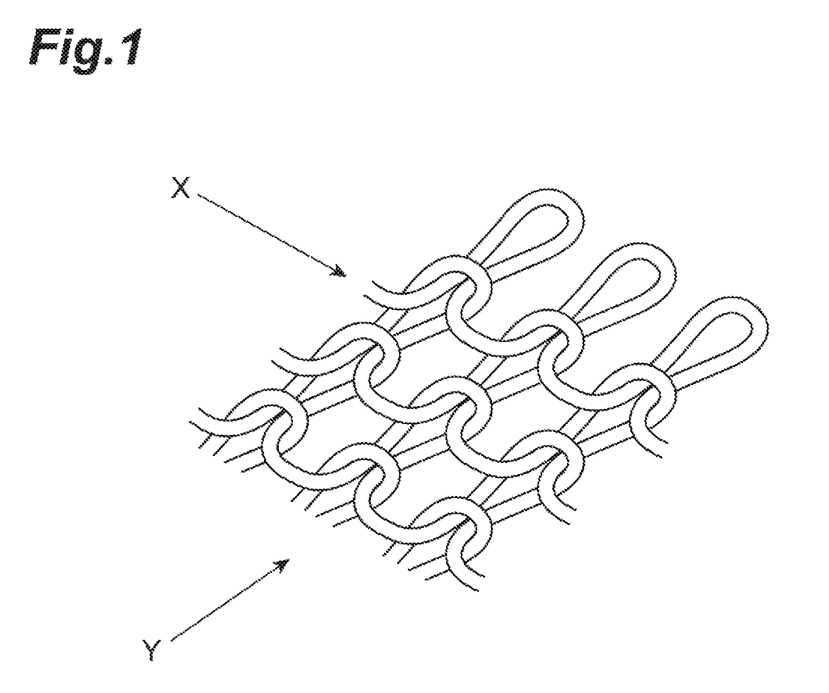
FIG. 1 is a perspective view showing the course direction and wale direction in a weft knitted fabric.
Figure 2:
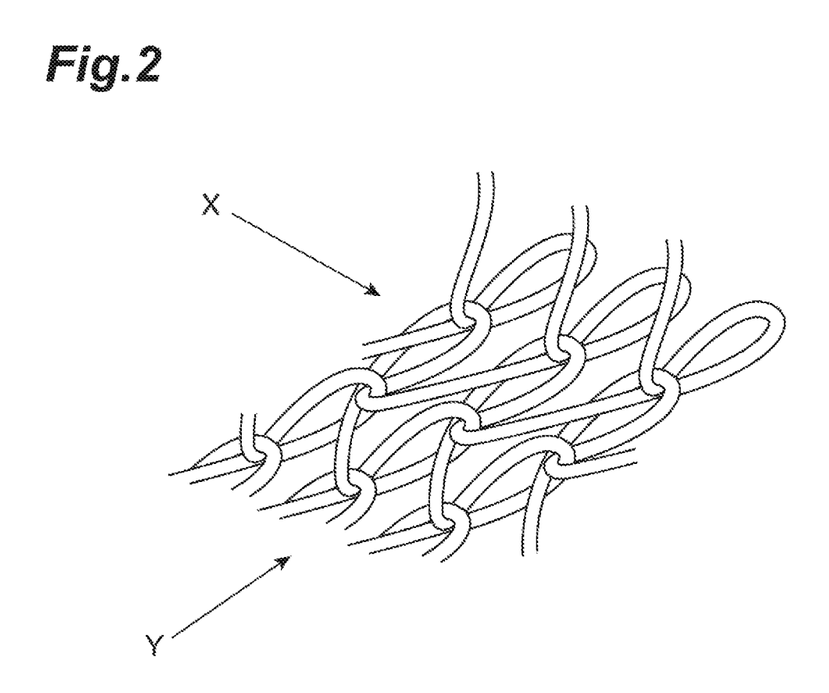
FIG. 2 is a perspective view showing the course direction and wale direction in a warp knitted fabric.

The knitted fabric preferably has a 50% modulus (load at 50% elongation) of 2 to 8 N/5 cm in the course direction and a 50% modulus of 2 to 12 N/5 cm in the wale direction. The course direction and wale direction of the knitted fabric will now be explained with reference to FIG. 1 and FIG. 2. FIG. 1 is a perspective view showing the course direction and wale direction in a weft knitted fabric, and FIG. 2 is a perspective view showing the course direction and wale direction in a warp knitted fabric. The direction indicated by X in FIG. 1 and FIG. 2 is the course direction, and it represents the weft direction of the knitted fabric. The direction indicated by Y in FIG. 1 and FIG. 2 is the wale direction, and it represents the warp direction of the knitted fabric. The modulus measuring method was according to JIS L 1096:2010. When the 50% modulus is lower than 2 N/5 cm in the course direction or wale direction, the knitted fabric may elongate when the adhesive mass is applied and the pressure-sensitive adhesive may seep into the stitches. Also, if the 50% modulus of the knitted fabric is higher than 8 N/5 cm in the course direction or 12 N/5 cm in the wale direction, the stretchability may be impaired, potentially impeding the ability to follow stretching of the skin when it is applied to joint parts.

Furthermore, the 50% elongation modulus of the knitted fabric is preferably 2 to 12 N/5 cm in the longitudinal direction (also known as the long axis direction) and 2 to 8 N/5 cm in the transverse direction (also known as the short axis direction or the cross-machine direction), when wound up into a roll before being cut to the size to be used as a support (the method of measuring the 50% elongation modulus being according to JIS L 1096:2010). With a 50% elongation modulus of lower than 2 N/5 cm in at least the longitudinal direction or the transverse direction, the knitted fabric may elongate when the adhesive mass is applied, causing the pressure-sensitive adhesive to seep into the stitches and potentially reducing the function of the gel patch. Also, if the 50% elongation modulus of the knitted fabric is higher than 12 N/5 cm in the longitudinal direction or 8 N/5 cm in the transverse direction, the stretchability may be impaired, potentially impeding the ability to follow stretching of the skin when it is applied to joint parts.

Spreading of the adhesive mass of the invention onto such a knitted fabric will allow attachment for longer periods.

The support is more preferably a knitted fabric with an interlocking rib stitch, and most preferably the basis weight of the knitted fabric is 95 to 125 g/m² and the thickness is 450 to 650 μm. A rib stitch knitted fabric has the front and back stitches knitted in the course direction, and therefore basically has no front/back. Also, rib stitch derivative weaves include half cardigan and full cardigan stitches. A rib stitch knitted fabric may be suitably used as the support from the viewpoint of excellent stretchability and improved anchorage of the pressure-sensitive adhesive layer. A rib stitch may be a circular knit or one knitted in a flat manner. A rib stitch knitted fabric tends to have excellent stretchability in the transverse direction. Moreover, if the thickness of the knitted fabric is within the range specified above, the stretchability and softness of the gel patch will be even more excellent.

A gel patch using such a knitted fabric as the support can be attached for a longer period. When an adhesive solution is to be spread onto a knitted fabric, it is preferably spread so that the range in which the adhesive mass infiltrates into the knitted fabric is within 23 to 40% of the thickness direction of the knitted fabric. If the infiltration of the adhesive mass into the knitted fabric is within such a range, there will be no seepage of water content in the adhesive solution from the surface of the support on the opposite side from the side contacting the adhesive layer. Furthermore, the gel patch obtained by spreading in this manner has even more excellent skin permeability of ketoprofen and skin migration of BM-DBM, by exhibiting an ODT (occlusive dressing technique) effect.

When a support with a thickness of about 0.55 to 0.8 mm is used, it will tend to be possible to better suppress seeping of components in the adhesive layer. In addition, if a support with a thickness of about 0.4 to 0.65 mm is used, this will lower the level difference due to the thickness of the gel patch when it is attached to skin, thereby helping to reduce peeling off during use and minimizing the effect on daily living activities such as donning and removal of clothing.

The adhesive layer of this embodiment is an aqueous adhesive mass comprising ketoprofen, BM-DBM and propylene glycol.

The mass of the adhesive layer of the gel patch is preferably 320 to 650 g/m² and more preferably 380 to 550 g/m². If the mass of the adhesive layer is 320 to 650 g/m², the fitted feel will be satisfactory and the adhesion can be improved for longer periods. If the mass of the adhesive layer is within the aforementioned range, it will be possible to reduce the thickness of the gel patch as a whole.

The thickness of the adhesive layer of this embodiment is preferably 0.4 to 1.0 mm, more preferably 0.5 to 0.8 mm and even more preferably 0.6 to 0.7 mm. Also, the thickness of the adhesive layer of this embodiment may be 0.2 to 1.0 mm, 0.3 to 0.8 mm, or 0.4 to 0.7 mm. If the thickness of the gel patch as a whole is 1.0 mm or smaller, it will more easily follow the skin and the level difference caused by the thickness of the gel patch when it is attached to the skin will be reduced, thus helping to prevent detachment even when the clothing, etc. is rubbed.

Throughout the present specification, "ketoprofen" means the compound represented by chemical formula (1) or a pharmaceutically acceptable salt thereof. Ketoprofen exists as two different optical isomers, the R-isomer and S-isomer. The ketoprofen used for this embodiment may be either of the optical isomers, or a mixture of the two optical isomers in any desired ratio may be used.

[Chemical Formula 1]

(1)

Pharmaceutically acceptable salts of ketoprofen include inorganic salts such as sodium salt, potassium salt and calcium salt, and amine salts such as monoethanolamine and diethanolamine.

The content of ketoprofen in the adhesive layer of this embodiment is 1.5 to 2.5 mass % and preferably 1.8 to 2.2 mass %, based on the mass of the adhesive layer as a whole.

Throughout the present specification, "4-tert-butyl-4'-methoxydibenzoylmethane" (BM-DBM) means the compound represented by chemical formula (2).

[Chemical Formula 2]

(2)

The content of BM-DBM in the adhesive layer of this embodiment is 1 to 5 mass %, preferably 1 to 3 mass % and more preferably 1.5 to 2.5 mass %, based on the mass of the adhesive layer as a whole. If the BM-DBM content is 1 mass % or greater, it will be possible to inhibit photodecomposition of ketoprofen by irradiation with light rays such as ultraviolet rays.

The content of propylene glycol in the adhesive layer of this embodiment is 5 to 20 mass %, preferably 10 to 20 mass %, more preferably 12 to 18 mass % and most preferably 14 to 16 mass %, based on the mass of the adhesive layer as a whole. If the propylene glycol content is 5 mass % or greater, it will be possible to exhibit the pharmacological effect of ketoprofen while increasing the skin migration properties of BM-DBM. If the propylene glycol content is 10 mass % or greater, it will be possible to exhibit the pharmacological effect of ketoprofen while further increasing the skin migration properties of BM-DBM.

The ketoprofen-containing gel patch of this embodiment may further comprise D-sorbitol.

The content of D-sorbitol in the adhesive layer of this embodiment is 10 to 20 mass %, preferably 12 to 18 mass % and more preferably 14 to 16 mass %, based on the mass of the adhesive layer as a whole. If the D-sorbitol content is 10 mass % or greater, it will be possible to exhibit the pharmacological effect of ketoprofen while increasing the skin migration properties of BM-DBM.

Other components may also be added to the adhesive layer. Such other components include pressure-sensitive adhesives, water-soluble polymers, solubilizers, antioxidants, humectants, cooling agents, inorganic powders, coloring agents, flavors and the like.

A pressure-sensitive adhesive is not particularly limited so long as it can increase the adhesive force of the gel patch, and any one commonly known to those skilled in the art may be used. The pressure-sensitive adhesive used may be an acrylate-based resin emulsion such as poly(methyl acrylate/2-ethylhexyl acrylate), and specifically, there may be mentioned the ULTRASOL Series such as ULTRASOL W-50 (trade name of Aica Kogyo Co., Ltd.), the PRIMAL Series such as PRIMAL N-580NF (trade name of Japan Acrylic Chemical), and the NIKASOL Series such as NIKASOL TS-620 (trade name of Nippon Carbide Industries Co., Inc.). The gel patch containing BM-DBM, according to this embodiment, can have even more greatly increased adhesion by further addition of an acrylic-based resin emulsion.

The water-soluble polymer is not particularly limited so long as it can retain water content in the gel patch, and any one commonly known to those skilled in the art may be used. Examples of water-soluble polymers include sodium polyacrylate, partially neutralized polyacrylic acid, polyacrylic acid, gelatin, polyvinyl alcohol, polyvinylpyrrolidone, polyethylene oxide, polyvinyl methacrylate, sodium alginate, hydroxypropyl cellulose, carboxymethyl cellulose sodium, methyl cellulose and carrageenan, any of which may be used alone or in combinations of two or more. Gelatin and polyvinyl alcohol are preferred as water-soluble polymers.

The water-soluble polymer content is preferably 1 to 40 mass %, based on the mass of the adhesive layer as a whole.

A solubilizer is not particularly limited so long as it can dissolve the drug, and examples include crotamiton; N-methylpyrrolidone; polyalkylene glycols such as polyethylene glycol and polybutylene glycol; and fatty acid esters such as isopropyl myristate, diethyl adipate and polyoxyalkylenesorbitan fatty acid esters. These solubilizers may be used alone or in combinations of two or more.

The solubilizer content is preferably 0 to 30 mass %, based on the mass of the adhesive layer as a whole.

Antioxidants include phenol derivatives such as butylhydroxyanisole, dibutylhydroxytoluene, thymol and propyl gallate, tocopherol and its ester derivatives, and ascorbic acid and its ester derivatives.

The antioxidant content is preferably 0 to 10 mass %, based on the mass of the adhesive layer as a whole.

The aforementioned humectants are not particularly limited so long as they can suppress evaporation of moisture from the adhesive layer with the passage of time. Examples of humectants include polyhydric alcohols such as concentrated glycerin, ethylene glycol, polyethylene glycol, liquid paraffin, 1,3-propanediol (propylene glycol) and 1,4-butanediol (butylene glycol). These humectants may be used alone or in combinations of two or more. The humectant is preferably concentrated glycerin.

The humectant content is preferably 0 to 60 mass %, based on the mass of the adhesive layer as a whole.

Examples of cooling agents include thymol, 1-menthol, dl-menthol and 1-isopulegol, among which 1-menthol is preferred for use.

The cooling agent content is preferably 0 to 15 mass %, based on the mass of the adhesive layer as a whole.

The gel patch may also comprise a release liner. The release liner is laminated on the adhesive layer, on the side opposite the support. If a release liner is provided, it will be possible to inhibit reduction in the water content of the adhesive layer during storage, tending to help reduce adhesion of dirt and the like onto the adhesive layer.

There are no particular restrictions on the material of the release liner, and the liner used may be one that is generally used by those skilled in the art. When a sheet or resin film is used as the release liner, the material may be, for example, polyethylene, polypropylene, polybutylene, polyethylene terephthalate, rayon, polyurethane, woodfree paper or a cellulose derivative, any of which may be used alone or in combinations of two or more. The material of the release liner is preferably a polypropylene film. The release liner may also be one that has been treated by embossing. Treatment of the release liner by embossing will help prevent lateral shifting. The thickness of the release liner is preferably 20 to 100 µm.

The gel patch may be stored inside a pouch. Storage inside a pouch can minimize reduction in the water content of the adhesive layer and can reduce adhesion of dirt and the like onto the adhesive layer.

(Method of Preparing Gel Patch)

Ketoprofen, BM-DBM and propylene glycol, with D-sorbitol and other components as necessary, were mixed and stirred for a prescribed time period to obtain an adhesive mass. The obtained adhesive mass is evenly spread onto the release liner so that the mass of the adhesive mass per gel patch (14 cm×10 cm) is a prescribed mass, and then a support is immediately laminated over it to prepare a gel patch.

EXAMPLES

The gel patch of the invention will now be explained in greater detail using examples and test examples, with the understanding that the invention is in no way limited to the examples. The contents listed in the following tables are expressed as mass %, unless otherwise specified. The method of preparing and evaluating the gel patches in the examples and comparative examples were as follows.

1. Hairless Mouse Skin Permeability Test (1)

The components listed in Table 1 were mixed, and then stirred for a prescribed period of time to obtain an adhesive mass. The obtained adhesive mass was evenly spread onto the release liner so that the mass of the adhesive mass was 10 g per gel patch (14 cm×10 cm), and then a nonwoven fabric was immediately laminated over it to prepare a gel patch for each of Reference Example 1 and Comparative Example 1. For preparation of the gel patches of Reference Example 1 and Comparative Example 1, the adhesive layer mass was 10 g/140 cm². Also, the contents of each of the components in Table 1 are listed as contents (mass %) based on the mass of the adhesive layer as a whole. Skin was excised from the back of a hairless mouse and set in a flow-through cell (0.785 cm²) with the dermis side facing the receptor layer side, and with exterior circulation of hot water at 37° C. The gel patches of Reference Example 1 and Comparative Example 1 were each attached to the horny layer side, and sampling was conducted every 4 hours up to 24 hours after attachment, at a rate of 0.8 mL/hr. In this test, physiological saline was used as the receptor layer. Also, the components listed in Table 2 and Table 3 were used to prepare tape preparations for Comparative Example 2 and Reference Examples 2 to 8, by a method known to those skilled in the art. Skin permeability testing was carried out by the same procedure, using the tape preparations of Comparative Example 2 and Reference Examples 2 to 8 instead of gel patches. For preparation of the tape preparations of Comparative Example 2 and Reference Examples 2 to 8, a woven fabric was used as the support and the mass of the adhesive layer was 1 g/70 cm². In Table 2 and Table 3, "SIS block copolymer" means styrene-isoprene-styrene block copolymer, and "SBR rubber" means styrene-butadiene copolymer.

TABLE 1

|  | Reference Example 1 | Comparative Example 1 |
|---|---|---|
| Ketoprofen | 2 | 0.3 |
| 1-Menthol | 0.3 | 0.3 |
| Gelatin | 2.5 | 2.5 |
| Glycerin | 30 | 30 |
| Partially neutralized polyacrylic acid | 4 | 4 |
| Polyvinyl alcohol | 2.5 | 2.5 |
| Purified water | 53.7 | 55.4 |
| Other components | 5 | 5 |
| Total | 100 | 100 |

TABLE 2

|  | Comparative Example 2 |
|---|---|
| Ketoprofen | 2 |
| 1-Menthol | 3 |
| BM-DBM | 2 |
| Hydrogenated rosin glycerin ester | 7.5 |
| SIS block copolymer | 23 |
| Polyisobutylene | 10 |
| Liquid paraffin | 47 |
| Other components | 5.5 |
| Total | 100 |

TABLE 3

|  | Reference Example 2 | Reference Example 3 | Reference Example 4 | Reference Example 5 |
|---|---|---|---|---|
| Ketoprofen | 2 | 2 | 2 | 2 |
| 1-Menthol | 3 | 3 | 3 | 3 |
| Hydrogenated rosin glycerin ester | 7.5 | — | 10 | — |
| Alicyclic saturated hydrocarbon resin | — | 7.5 | — | — |
| SIS block copolymer | 23 | 23 | 23 | — |
| SBR rubber | — | — | — | 13 |
| Natural rubber | — | — | — | 10 |
| Polyisobutylene | 10 | 10 | — | — |
| Polybutene | — | — | 10 | 10 |
| Acrylate-based resin emulsion | — | — | — | 5 |
| Liquid paraffin | 47 | 47 | 44.5 | 48.5 |
| Other components | 7.5 | 7.5 | 7.5 | 8.5 |
| Total | 100 | 100 | 100 | 100 |

|  | Reference Example 6 | Reference Example 7 | Reference Example 8 |
|---|---|---|---|
| Ketoprofen | 2 | 2 | 2 |
| 1-Menthol | 3 | 3 | 3 |
| Hydrogenated rosin glycerin ester | — | — | 12 |

TABLE 3-continued

| | | | |
|---|---|---|---|
| Alicyclic saturated hydrocarbon resin | 7.5 | — | — |
| SIS block copolymer | 26 | — | 20 |
| SBR rubber | — | 10 | — |
| Natural rubber | — | 13 | — |
| Polyisobutylene | 10 | — | 10 |
| Polybutene | — | 10 | — |
| Acrylate-based resin emulsion | — | 5 | — |
| Liquid paraffin | 44 | 48 | 46 |
| Other components | 7.5 | 9 | 7 |
| Total | 100 | 100 | 100 |

Table 4 shows the cumulative skin permeation ($\mu g/cm^2$) of ketoprofen during the period up to 24 hours after attachment, for the gel patches of Reference Example 1 and Comparative Example 1. The gel patch of Comparative Example 1 had lower cumulative skin permeation than the tape preparation of Comparative Example 2. Also, the gel patches of Reference Example 1 and Comparative Example 1 exhibited about the same level of cumulative skin permeation. It was thus demonstrated that cumulative skin permeation does not increase even with increased ketoprofen content in the gel patch of Comparative Example 1.

TABLE 4

| | Reference Example 1 | Comparative Example 1 | Comparative Example 2 |
|---|---|---|---|
| Cumulative skin permeation [$\mu g/cm^2$] | 24 | 26 | 131 |

2. Hairless Mouse Skin Permeability Test (2) The components listed in Table 5 were mixed, and then stirred for a prescribed period of time to obtain an adhesive solution. The obtained adhesive solution was evenly spread onto the release liner so that the mass of the adhesive mass was 7 g per gel patch (14 cm×10 cm), and then a nonwoven fabric was immediately laminated over it to prepare a gel patch for each of Reference Example 9 and Comparative Examples 3 to 7. For preparation of each gel patch, the mass of the adhesive layer was 7 g/140 cm$^2$. The cumulative skin permeation was calculated for each of the obtained gel patches of Reference Example 9 and Comparative Examples 3 to 7, and the tape preparation of Comparative Example 2, in the similar manner as hairless mouse skin permeability test (1).

TABLE 5

| | Reference Example 9 | Comparative Example 3 | Comparative Example 4 |
|---|---|---|---|
| Ketoprofen | 2 | 2 | 2 |
| 1-Menthol | 0.3 | 0.3 | 0.3 |
| Crotamiton | 2.5 | 2 | 2 |
| Partially neutralized polyacrylic acid | 4 | 4 | 4 |
| Polyvinyl alcohol | 2.5 | 2.5 | 2.5 |
| Glycerin | 30 | 30 | 30 |
| Propylene glycol | 15 | — | — |
| Polyethylene glycol 400 | — | 15 | — |
| Butylene glycol | — | — | 15 |
| Ethanol | — | — | — |
| Purified water | 36.95 | 36.95 | 36.95 |
| Other components | 6.75 | 7.25 | 7.25 |
| Total | 100 | 100 | 100 |

TABLE 5-continued

| | Comparative Example 5 | Comparative Example 6 | Comparative Example 7 |
|---|---|---|---|
| Ketoprofen | 2 | 2 | 2 |
| 1-Menthol | 0.3 | 0.3 | 0.3 |
| Crotamiton | 2 | 5 | 2 |
| Partially neutralized polyacrylic acid | 4 | 4 | 4 |
| Polyvinyl alcohol | 2.5 | 2.5 | 2.5 |
| Glycerin | 30 | 30 | 30 |
| Propylene glycol | — | — | — |
| Polyethylene glycol 400 | — | — | — |
| Butylene glycol | — | — | — |
| Ethanol | 5 | — | — |
| Purified water | 46.95 | 48.95 | 51.95 |
| Other components | 7.25 | 7.25 | 7.25 |
| Total | 100 | 100 | 100 |

Table 6 shows the cumulative skin permeation ($\mu g/cm^2$) of ketoprofen during the period up to 24 hours after attachment, for the gel patches of Reference Example 9 and Comparative Examples 3 to 7 and the tape preparation of Comparative Example 2. When the gel patch of Reference Example 9 was used, the 24-hour cumulative skin permeation of ketoprofen was higher than the 24-hour cumulative skin permeation of ketoprofen when using the tape preparation of Comparative Example 2. The gel patch of Comparative Example 4 had seepage of the components in the adhesive layer through the support, such that the cumulative skin permeation could not be measured.

TABLE 6

| | Reference Example 9 | Comp. Example 3 | Comp. Example 4 | Comp. Example 5 |
|---|---|---|---|---|
| Cumulative skin permeation [$\mu g/cm^2$] | 164 | 100 | — | 96 |

| | Comp. Example 6 | Comp. Example 7 | Comp. Example 2 |
|---|---|---|---|
| Cumulative skin permeation [$\mu g/cm^2$] | 60 | 35 | 131 |

3. Guinea Pig Skin Migration Test The components listed in Table 7 were mixed, and then stirred for a prescribed period of time to obtain an adhesive mass. The obtained adhesive mass was evenly spread onto a release liner, and then a nonwoven fabric was immediately laminated over it to prepare a gel patch for Example 1. For preparation of the gel patch of Example 1, the mass of the adhesive layer was 7 g/140 cm$^2$. Also, for acrylate resin emulsion 1 there was used ULTRASOL W-50 (trade name of Aica Kogyo Co., Ltd.) and for acrylate resin emulsion 2 there was used NIKASOL TS-620 (trade name of Nippon Carbide Industries Co., Inc.). The gel patch of Example 1 was applied onto the back skin of a guinea pig, and after 4 hours the gel patch was released. The skin at the site of application of the gel patch was excised, the skin slice was extracted with methanol, and high-performance liquid chromatography (HPLC) was used to calculate the ketoprofen and BM-DBM concentrations ($\mu g/cm^2$) in the obtained skin slice. The same procedure was also carried out for the tape preparation containing 2 mass % ketoprofen (Comparative Example 2), and the ketoprofen and BM-DBM concentrations were calculated.

TABLE 7

|  | Example 1 | Example 2 | Example 3 | Example 4 |
| --- | --- | --- | --- | --- |
| Ketoprofen | 2 | 2 | 2 | 2 |
| BM-DBM | 2 | 2 | 2 | 2 |
| Propylene glycol | 15 | 15 | 13 | 17 |
| D-Sorbitol | — | 15 | — | 13 |
| Butylene glycol | — | — | — | — |
| l-Menthol | 0.3 | 0.3 | 0.3 | 0.3 |
| Crotamiton | 2.5 | 2.5 | 2 | 2 |
| Polyacrylic acid starch | — | — | — | — |
| Partially neutralized polyacrylic acid | 4 | 4 | 4 | 4 |
| Carboxymethyl cellulose Sodium | — | — | — | — |
| Carboxyvinyl polymer | — | — | — | 1 |
| Polyvinyl alcohol | 2.5 | 2.5 | 2.5 | 2.5 |
| Glycerin | 15 | 5 | 15 | 5 |
| Acrylate-based resin emulsion 1 | — | — | 16.67 | 16.67 |
| Acrylate-based resin emulsion 2 | 16.67 | 16.67 | — | — |
| Purified water | 33.98 | 28.48 | 35.58 | 30 |
| Other components | 6.05 | 6.55 | 6.95 | 4.53 |
| Total | 100 | 100 | 100 | 100 |

|  | Example 5 | Example 6 | Example 7 | Example 8 |
| --- | --- | --- | --- | --- |
| Ketoprofen | 2 | 2 | 2 | 2 |
| BM-DBM | 2 | 2 | 2 | 2 |
| Propylene glycol | 15 | 16 | 15 | 15 |
| D-Sorbitol | — | 14 | 15 | — |
| Butylene glycol | — | — | 14 | — |
| l-Menthol | 0.3 | 0.3 | 0.3 | 0.3 |
| Crotamiton | 1 | 1 | 3 | 3 |
| Polyacrylic acid starch | — | — | 0.5 | — |
| Partially neutralized polyacrylic acid | 6.5 | 4 | 5 | 5 |
| Carboxymethyl cellulose Sodium | 3 | 2 | — | 3 |
| Carboxyvinyl polymer | 2 | 2 | — | — |
| Polyvinyl alcohol | 5 | 2.5 | — | — |
| Glycerin | 20 | 10 | — | 20 |
| Acrylate-based resin emulsion 1 | — | — | — | — |
| Acrylate-based resin emulsion 2 | — | — | — | — |
| Purified water | 32.8 | 34.3 | 38.2 | 35 |
| Other components | 10.4 | 9.9 | 5 | 14.7 |
| Total | 100 | 100 | 100 | 100 |

Table 8 shows the ketoprofen and BM-DBM concentrations for the gel patch of Example 1 and the tape preparation of Comparative Example 2. The concentration of ketoprofen in the skin slice when using the gel patch of Example 1 was approximately the same as when using the tape preparation of Comparative Example 2. However, the concentration of BM-DBM in the skin slice when using the gel patch of Example 1 was higher than when using the tape preparation of Comparative Example 2. Thus, the gel patch of Example 1 may be said to have more excellent skin migration of BM-DBM than the tape preparation of Comparative Example 2.

TABLE 8

|  | Example 1 | Comparative Example 2 |
| --- | --- | --- |
| Ketoprofen concentration | 16.5 | 14.0 |
| BM-DBM concentration | 2.5 | 0.7 |

4. Photosensitizing Test The components listed in Table 7 were mixed, and then stirred for a prescribed period of time to obtain an adhesive mass. The obtained adhesive mass was evenly spread onto a release liner, and then a nonwoven fabric was immediately laminated over it to prepare a gel patch for Examples 2 to 8. For preparation of the gel patches of Examples 2 to 8, the mass of the adhesive layer was 10 g/140 cm$^2$. Of the obtained gel patches, for Examples 1 and 2, a photosensitizing test was conducted by slight modification of the "Adjuvant and strip method" using guinea pigs (Sato et al., Nishinihon Journal of Dermatology 42, 831-837(1980)). Specifically, the dorsocervical regions of Hartley white female guinea pigs (6 per group) were shaved, and the gel patches of Examples 1 and 2 and the tape preparation of Comparative Example 2 were attached at the 4 corners of a 2 cm×2 cm square area of the dorsocervical region (photosensitizing treatment), and after 1 hour, were irradiated with ultraviolet A rays (also known as "UVA", exposure energy: 10 J/cm$^2$). The photosensitizing treatment was carried out continuously for 5 days. From the first day to 3 weeks after photosensitizing treatment, the dorsolumbar regions of the guinea pigs were shaved, and the gel patches of Examples 1 and 2 and the tape preparation of Comparative Example 2 were attached at the 4 corners of a 2 cm×2 cm square area at a different site from that used for the photosensitizing treatment, and after 1 hour, were irradiated with UVA (exposure energy: 10 J/cm$^2$) (photostimulation treatment). The skin reactions (erythema and edema) after 24 hours and after 48 hours from UVA irradiation were evaluated based on the aforementioned criteria of Sato et al.

The mean values for the obtained skin reaction scores based on the evaluation criteria of Sato et al. are shown in Table 9. In Table 9, "UVA(+)" indicates irradiation with UVA, and "UVA(−)" indicates no irradiation with UVA.

Virtually no skin irritation was found with the gel patch of Example 1. Also, the gel patch of Example 1 had improved photosensitization despite the high concentration of ketoprofen in the skin slice even compared to the tape preparation of Comparative Example 2. Also, the gel patch of Example 2 which contained D-sorbitol had even more markedly improved photosensitization than the gel patch of Example 1. Similar effects were also found for Examples 3 to 8.

TABLE 9

| Test substance | | Mean skin reaction score | | | |
| --- | --- | --- | --- | --- | --- |
| Photo-sensitizing treatment | Photo-stimulation treatment | UVA(+) | | UVA(−) | |
| | | After 24 hours | After 48 hours | After 24 hours | After 48 hours |
| Untreated | Example 1 | 0.0 | 0.0 | 0.0 | 0.0 |
| | Example 2 | 0.0 | 0.0 | 0.0 | 0.0 |
| | Comparative Example 2 | 0.0 | 0.0 | 0.0 | 0.0 |
| Example 1 | Example 1 | 1.2 | 2.0 | 0.0 | 0.0 |
| | Comparative Example 2 | 2.5 | 2.8 | 0.0 | 0.0 |
| Example 2 | Example 2 | 0.4 | 1.3 | 0.0 | 0.0 |
| | Comparative Example 2 | 1.4 | 2.0 | 0.0 | 0.0 |

The invention claimed is:

1. A gel patch comprising a support and an adhesive layer on the support, wherein the adhesive layer comprises 1.5 to 2.5 mass % of ketoprofen, 1.5 to 2.5 mass % of 4-tert-butyl-4'-methoxydibenzoylmethane and 12 to 18 mass % of propylene glycol, based on the total mass of the adhesive layer.

2. The gel patch according to claim 1, wherein the adhesive layer further comprises 12 to 18 mass % of D-sorbitol based on the total mass of the adhesive layer.

3. The gel patch according to claim 1, wherein the support is a knitted fabric with a thickness of 450 to 650 μm.

4. The gel patch according to claim 2, wherein the support is a knitted fabric with a thickness of 450 to 650 μm.

5. The gel patch according to claim 1, wherein the adhesive layer further comprises a pressure sensitive adhesive, and the pressure-sensitive adhesive comprises poly(methyl acrylate/2-ethylhexyl acrylate).

6. The gel patch according to claim 1, wherein the adhesive layer has a mass of 320 to 650 g/m$^2$.

7. The gel patch according to claim 1, wherein the adhesive layer has a thickness of 0.4 to 1.0 mm.

8. The gel patch according to claim 1, wherein the support has an elongation recovery rate of 70 to 90% after 50% elongation.

9. The gel patch according to claim 1, wherein the support is a knitted fabric, and the knitted fabric has a basis weight of 80 to 150 g/m$^2$.

10. The gel patch according to claim 1, wherein the support is a knitted fabric having a course direction and a wale direction, and the knitted fabric has 50% modulus (load at 50% elongation) of 2 to 8 N/5 cm in the course direction and a 50% modulus of 2 to 12 N/5 cm in the wale direction.

11. The gel patch according to claim 1, wherein the support is a knitted fabric having an interlocking rib stitch, and the knitted fabric has a basis weight of 95 to 125 g/m$^2$.

12. The gel patch according to claim 1, wherein the support is a knitted fabric having a thickness, and the adhesive layer infiltrates into the knitted fabric by 23 to 40% of the thickness of the knitted fabric.

\* \* \* \* \*

UNITED STATES PATENT AND TRADEMARK OFFICE
CERTIFICATE OF CORRECTION

PATENT NO. : 9,707,194 B2
APPLICATION NO. : 15/121534
DATED : July 18, 2017
INVENTOR(S) : Seiichiro Tsuru et al.

It is certified that error appears in the above-identified patent and that said Letters Patent is hereby corrected as shown below:

In the Claims

Claim 1, Column 12, Line 62, please replace the word "hutyl" with "butyl".

Signed and Sealed this
Fifth Day of September, 2017

Joseph Matal
*Performing the Functions and Duties of the*
*Under Secretary of Commerce for Intellectual Property and*
*Director of the United States Patent and Trademark Office*